US005578563A

United States Patent [19]
Trinh et al.

[11] Patent Number: 5,578,563
[45] Date of Patent: Nov. 26, 1996

[54] COMPOSITION FOR REDUCING MALODOR IMPRESSION ON INANIMATE SURFACES

[75] Inventors: Toan Trinh, Maineville; Jerome P. Cappel, Cincinnati; Philip A. Geis, West Chester; Mark L. McCarty, Loveland; Susan S. Zwerdling, Wyoming, all of Ohio

[73] Assignee: The Procter & Gamble Company, Cincinnati, Ohio

[21] Appl. No.: 289,733

[22] Filed: Aug. 12, 1994

[51] Int. Cl.[6] .................................. C11D 7/26; C11D 7/12
[52] U.S. Cl. ...................... 510/513; 510/103; 424/76.1
[58] Field of Search ................................. 252/156, 173, 252/174.11, 174.14, 174.17, 174.23; 424/76.1

[56] References Cited

U.S. PATENT DOCUMENTS

| | | | |
|---|---|---|---|
| D. 244,991 | 7/1977 | Weckman et al. | D9/63 |
| D. 275,078 | 8/1984 | Wassergord et al. | D9/300 |
| D. 277,978 | 3/1985 | Bundschuh | D23/17 |
| 2,544,093 | 3/1951 | Kilgore | 252/1 |
| 3,074,891 | 1/1963 | Kulka | 252/305 |
| 3,172,817 | 3/1965 | Leupold et al. | 167/90 |
| 3,426,011 | 2/1969 | Parmerter et al. | 260/209 |
| 3,436,776 | 4/1969 | Davis | 9/8 |
| 3,453,257 | 7/1969 | Parmerter et al. | 260/209 |
| 3,453,258 | 7/1969 | Parmerter et al. | 260/209 |
| 3,453,259 | 7/1969 | Parmerter et al. | 260/209 |
| 3,453,260 | 7/1969 | Parmerter et al. | 260/209 |
| 3,459,731 | 8/1969 | Gramera et al. | 260/209 |
| 3,553,191 | 1/1971 | Parmerter et al. | 260/209 |
| 3,565,887 | 2/1971 | Parmerter et al. | 260/234 |
| 3,600,325 | 8/1971 | Kaufman et al. | 252/305 |
| 4,082,223 | 4/1978 | Nozawa | 239/333 |
| 4,161,288 | 7/1979 | McKinney | 239/333 |
| 4,265,899 | 5/1981 | Lewis et al. | 424/270 |
| 4,267,166 | 5/1981 | Yajima | 424/48 |
| 4,274,560 | 6/1981 | Cater | 222/321 |
| 4,299,749 | 11/1981 | McCarthy et al. | 260/29.6 Z |
| 4,325,939 | 4/1982 | Shah | 424/55 |
| 4,434,917 | 3/1984 | Saito et al. | 222/383 |
| 4,449,987 | 5/1984 | Lindauer | 44/7.5 |
| 4,469,674 | 9/1984 | Shah et al. | 424/52 |
| 4,535,152 | 8/1985 | Szejtli et al. | 536/103 |
| 4,558,821 | 12/1985 | Tada et al. | 239/333 |
| 4,616,008 | 10/1986 | Hirai et al. | 514/200 |
| 4,638,058 | 1/1987 | Brandt et al. | 536/103 |
| 4,678,598 | 7/1987 | Ogino et al. | 252/174.17 |
| 4,693,890 | 9/1987 | Wilson et al. | 424/78 |
| 4,696,676 | 9/1987 | Wilson et al. | 44/7.5 |
| 4,727,824 | 3/1988 | Ducharme et al. | 119/1 |
| 4,735,347 | 4/1988 | Schultz et al. | 222/321 |
| 4,746,734 | 5/1988 | Tsuchiyama et al. | 536/103 |
| 4,779,803 | 10/1988 | Corsette | 239/428.5 |
| 4,818,524 | 4/1989 | Gibbs | 424/76.1 |
| 4,819,835 | 4/1989 | Tasaki | 222/383 |
| 4,895,279 | 1/1990 | Schultz | 222/321 |
| 4,933,371 | 6/1990 | Hink et al. | 514/739 |
| 4,946,672 | 8/1990 | Gibbs | 424/76.1 |
| 5,102,564 | 4/1992 | Gardlik et al. | 252/8.9 |
| 5,111,971 | 5/1992 | Winer | 222/95 |
| 5,196,200 | 3/1993 | Wilson et al. | 424/411 |
| 5,232,126 | 8/1993 | Winer | 222/95 |
| 5,234,610 | 8/1993 | Gardlik et al. | 252/8.6 |
| 5,234,611 | 8/1993 | Trinh et al. | 252/8.8 |
| 5,303,867 | 4/1994 | Peterson | 239/333 |
| 5,376,363 | 12/1994 | Benfatto et al. | 424/66 |

FOREIGN PATENT DOCUMENTS

| | | | |
|---|---|---|---|
| 53-41440 | 4/1978 | Japan | A61K 7/32 |
| 53-041440-A | 4/1978 | Japan | A61K 7/32 |
| 58-124452 | 7/1983 | Japan | A61L 9/01 |
| 61-128973 | 6/1986 | Japan | A61L 9/01 |

(List continued on next page.)

OTHER PUBLICATIONS

"Semio Activity of Flavor and Fragrance Molecules on Various Insect Species", B. D. Mookherjee, et al., *Bioactive Volatile Compounds from Plants*, 1993 ACS Symposium Series, pp. 35–48.

Effects of Water and Alcohol on the formation of inclusion complexes of d–limonene and cyclodextrins, T. Furuta, et al., *Supramolecular Chemistry*, vol. 1, pp. 321–325, Jul. 30, 1992.

Studies on the Industrial Production and Application of Cyclodextrins, *Denpun Kagaku*, vol. 36, No. 1, pp. 35–42 (1989).

Interaction between Preservatives and 2–Hydroxypropyl–β–Cyclodextrin, T. Loftsson, et al., *Drug Development and Industrial Pharmacy*, 18(13), 1477–1484, (1992).

Interactions between p–hydroxybenzoic acid esters and hydroxypropyl–β–cylcodextrin and their antimicrobial effect against *Candida albicans*, S. J. Lehner, et al., Department of Pharmaceutics and Biopharmaceutics, Christian Albrecht University, (1992).

Powdery Encapsulation of d–Limonese by Kneading with Mixed Powders of β–Cyclodextrin and Maltodextrin at Low Water Content, T. Furuta, et al., Department of Biotechnology Tottori University, Sep. 21, 1993.

Effect of Hydroxypropyl–β–cyclodextrin on the Antimicrobial Action of Preservatives, S. J. Lehner, et al., *J. Pharm. Pharmacol*, 1994, 46: 186–191.

*Primary Examiner*—Paul Lieberman
*Assistant Examiner*—Caroline L. Dusheck
*Attorney, Agent, or Firm*—Robert B. Aylor

[57] ABSTRACT

The present invention relates to an aqueous composition for reducing malodor impression. The composition comprises from about 0.1% to about 20%, by weight of the composition, of solubilized, water-soluble alkali metal salt selected from the group consisting of carbonate salts, bicarbonate salts, and mixtures thereof, from about 0.01% to about 1%, by weight of the composition, of perfume. Optionally, but preferably, the composition comprises from about 0% to about 5%, by weight of the composition, of solubilized, water-soluble cyclodextrin, and from about 0% to about 3%, by weight of the composition, of solubilizing aid. The composition is essentially free of any material that would soil or stain fabric and contains less than about 5%, by weight of the composition, of low molecular weight monohydric alcohol, and has a pH of from about 7.5 to about 10.5.

21 Claims, No Drawings

FOREIGN PATENT DOCUMENTS

| | | | |
|---|---|---|---|
| 63-164953 | 7/1988 | Japan . | |
| 1-256597 | 10/1989 | Japan . | |
| 01256596A | 10/1989 | Japan | C11D 3/38 |
| 02251681A | 10/1990 | Japan . | |
| 3-170415 | 7/1991 | Japan | A61K 7/32 |
| 03170415A | 7/1991 | Japan | A61K 7/32 |
| 3-284616 | 12/1991 | Japan | A61K 7/16 |
| 941105 | 11/1963 | United Kingdom . | |
| 89/02698 | 4/1989 | WIPO | A01K 1/015 |
| 91/12029 | 8/1991 | WIPO | A61L 9/01 |

COMPOSITION FOR REDUCING MALODOR IMPRESSION ON INANIMATE SURFACES

TECHNICAL FIELD

The present invention relates to aqueous, preferably clear, composition for reducing malodor impression, comprising water-soluble alkali metal bicarbonate and/or carbonate salt, perfume and optionally, but preferably, solubilized, water-soluble cyclodextrin. The composition is designed to reduce malodor, i.e., freshen surfaces, especially, clothes e.g., those that are contaminated with environmental odors such as food odors, tobacco odors, and/or that are wetted with perspiration. Preferably the composition is used to restore and/or maintain freshness by reducing malodor without the need for washing or dry cleaning.

BACKGROUND OF THE INVENTION

The present invention relates to an aqueous, preferably clear, composition, article of manufacture, and method for use as a freshening composition. Preferably, the composition is sprayed onto fabrics, particularly clothes, to restore their freshness by reducing malodor impression, without washing or dry cleaning. Fabrics treated with the composition of the present invention also release extra fragrance upon rewetting, such as when the wearer perspires. The freshening composition of the present invention is designed to extend the wear of fabrics between washing or dry cleaning. Fabrics treated with the freshening composition of the present invention will stay fresher longer, and receive extra freshening effect via perfume release when it is most needed, that is upon fabric rewetting.

A wide variety of deodorizing compositions are known in the art, the most common of which only contain a perfume to mask the malodor. Odor masking is the intentional concealment of one odor by the addition of another. The preference to the masking perfume is varied greatly, depending on the application, e.g., underarm odor masking, fabric odor masking, bathroom odor masking, etc. Appropriate perfume ingredients need to be selected to connote freshness.

Odor modification, in which the odor is changed, e.g., by chemical modification, has also been used. Current malodor modification methods known in the art which do not simply mask odors are oxidative degradation, which uses oxidizing agents such as oxygen bleaches, chlorine, chlorinated materials such as sodium hypochlorite, chlorine dioxide, etc., and potassium permanganate to reduce malodor, and reductive degradation which uses reducing agents such as sodium bisulfite to reduce malodor. Both of these methods are unacceptable for use on fabrics because they can damage colored fabrics, specifically, they can bleach and discolor colored fabrics.

Other methods of odor control contain actives that are targeted to react with malodors having specific chemical functional groups. Examples of such actives are: biguanide polymers, which complex with organic compounds containing organically bound N and/or S atoms and fatty alcohol esters of methyl methacrylic acid which react with thiols, amines, and aldehydes. A more detailed description of these methods can be found in U.S. Pat. Nos. 2,544,093, 3,074, 891, and U.K. Pat. App. No. 941,105, all of said patents and applications are incorporated herein by reference. Fatty alcohol esters of methyl methacrylic acid are not preferred in the composition of this invention because they are not water soluble.

Other types of deodorizing compositions known in the art contain antibacterial and antifungal agents which regulate the malodor-producing microorganisms found on the surface to which the deodorizing composition is directed. Many skin deodorant products use this technology. These compositions are not effective on malodors that do not come from bacterial sources, such as tobacco or food odors.

Fabric malodor is most commonly caused by environmental odors such as tobacco odor, cooking and/or food odors, or body odor. The unpleasant odors are mainly organic molecules which have different structures and functional groups. One type of malodor that is very noticeable, and is commonly found on worn fabrics is low molecular weight, straight-chain, branched, and unsaturated $C_6$-$C_{11}$ fatty acids that cause axillary odor. See "Analysis of Characteristic Odor from Human Male Axillae", X. Zeng, et al., J. Chem. Ecol., pp. 1469–1492, 1991, incorporated herein by reference. See also, U.S. Pat. No. 4,664,909, Marschner et al., issued May 12, 1987, BE 830,098, published Oct. 1, 1975, and CA 1,088,428, published Oct. 28, 1980, DE 2,803,176, published Aug. 3, 1978, all of said patents and applications incorporated herein by reference.

Cyclodextrin molecules are known for their ability to form complexes with perfume ingredients and have typically been taught as a perfume carrier. The prior art teaches the use of drier-added fabric softener sheets containing high levels of cyclodextrin/perfume complexes wherein the fabrics treated with this solid cyclodextrin complex release perfume when the fabrics are rewetted. The art also teaches that cyclodextrin/perfume complexes used in aqueous rinse-added fabric softener compositions must be protected, e.g., with a hydrophobic wax coating so the cyclodextrin/perfume complexes will not decompose due to the presence of water. See U.S. Pat. No. 5,102,564 Gardlik et al., issued Apr. 7, 1992; U.S. Pat. No. 5,234,610, Gardlik et al., issued Aug. 10, 1993; U.S. Pat. No. 5,234,611 Trinh, et al., issued Aug. 10, 1993, all of said patents incorporated herein by reference. It is therefore highly surprising and unexpected to find that fabrics treated with the aqueous compositions of the present invention, which contain low levels of cyclodextrin, also exhibit perfume release upon rewetting. This phenomenon creates a benefit in that fabrics treated with the composition of the present invention will thus remain fresh longer, via a perfume release, when said fabrics are rewetted, such as when the wearer perspires.

SUMMARY OF THE INVENTION

The present invention relates to an aqueous composition for reducing malodor impression, comprising:

A. from about 0.1% to about 20%, by weight of the composition, of solubilized, water-soluble alkali metal salt selected from the group consisting of carbonate salts, bicarbonate salts, and mixtures thereof;

B. from about 0.01% to about 1%, by weight of the composition, of perfume;

C. from about 0% to about 5%, by weight of the composition, of solubilized, water-soluble cyclodextrin;

D. from about 0% to about 3%, by weight of the composition, of solubilizing aid; and E. aqueous carrier; and wherein said composition is essentially free of any material that would soil or stain fabric and wherein the composition contains less than about 5%, by weight of the composition, of low molecular weight monohydric alcohol, and wherein the pH of said composition is from about 7.5 to about 10.5.

The composition can be incorporated into a spray dispenser to create an article of manufacture that can facilitate treatment of inanimate articles and/or surfaces with an effective level of the composition in order to reduce malodor impression, yet not to be discernible when dried on the surface.

DETAILED DESCRIPTION OF THE INVENTION

The present invention relates to an aqueous composition for reducing malodor impression, comprising:

A. from about 0.1% to about 20%, by weight of the composition, of solubilized, water-soluble alkali metal salt selected from the group consisting of carbonate salts, bicarbonate salts, and mixtures thereof;

B. from about 0.01% to about 1%, by weight of the composition, of perfume;

C. from about 0% to about 5%, by weight of the composition, of solubilized, water-soluble cyclodextrin;

D. from about 0% to about 3%, by weight of the composition, of solubilizing aid; and E. aqueous carrier; and wherein said composition is essentially free of any material that would soil or stain fabric, wherein said composition contains less than about 5%, by weight of the composition, of low molecular weight monohydric alcohol, and wherein the pH of said composition is from about 7.5 to about 10.5.

I. COMPOSITION

(A). Soluble Carbonate and/or Bicarbonate Salts

Water-soluble alkali metal carbonate and/or bicarbonate salts, such as sodium bicarbonate, potassium bicarbonate, potassium carbonate, cesium carbonate, sodium carbonate, and mixtures thereof, are added to the composition of the present invention in order to help to control acid-type odors. Preferred salts are sodium carbonate monohydrate, potassium carbonate, sodium bicarbonate, potassium bicarbonate, and mixtures thereof. Solubilized, water-soluble alkali metal carbonate and bicarbonate salts are typically present at a level of from about 0.1% to about 20%, preferably from about 0.2% to about 10%, more preferably from about 0.3% to about 7%0, by weight of the composition. Compositions with higher concentrations of alkali metal salt can leave unacceptable visible powder and/or stains on fabrics as the solution evaporates off of the fabrics. This is especially a problem on dark-colored fabrics. It is preferable that incompatible metal salts, e.g., Ca, Zn, Fe, Ba, not be present because these ions can form water-insoluble carbonate and/or bicarbonate salts. The pH of the aqueous solutions of the present invention is preferably between about 7.5 to about 10.5, more preferably from about 8 to about 10. If carbonate salts are used, it may be necessary to adjust the pH to the preferred pH ranges.

(B). Perfume

The perfume selected for use in the fabric freshening composition of the present invention contains ingredients with odor characteristics which are preferred in order to provide a fresh impression on the surface to which the composition is directed, preferably those which provide a fresh impression for fabrics.

Preferably, at least about 25%, more preferably at least about 50%, most preferably at least about 75%, by weight of the perfume is composed of fragrance material selected from the group consisting of aromatic and aliphatic esters having molecular weights from about 130 to about 250; aliphatic and aromatic alcohols having molecular weights from about 90 to about 240; aliphatic ketones having molecular weights from about 150 to about 260; aromatic ketones having molecular weights from about 150 to about 270; aromatic and aliphatic lactones having molecular weights from about 130 to about 290; aliphatic aldehydes having molecular weights from about 140 to about 200; aromatic aldehydes having molecular weights from about 90 to about 230; aliphatic and aromatic ethers having molecular weights from about 150 to about 270; and condensation products of aldehydes and amines having molecular weights from about 180 to about 320; and essentially free from nitromusks and halogenated fragrance materials.

More preferably, at least about 25%, more preferably at least about 50%, most preferably at least about 75%, by weight of the perfume is composed of fragrance material selected from the group consisting of:

| Common Name | Chemical Type | Chemical Name | Approx. M.W. |
| --- | --- | --- | --- |
| adoxal | aliphatic aldehyde | 2,6,10-trimethyl-9-undecen-1-al | 210 |
| allyl amyl glycolate | ester | allyl amyl glycolate | 182 |
| allyl cyclohexane propionate | ester | allyl-3-cyclohexyl propionate | 196 |
| amyl acetate | ester | 3-methyl-1-butanol acetate | 130 |
| amyl salicylate | ester | amyl salicylate | 208 |
| anisic aldehyde | aromatic aldehyde | 4-methoxy benzaldehyde | 136 |
| aurantiol | schiff base | condensation product of methyl anthranilate and hydroxycitronellal | 305 |
| bacdanol | aliphatic alcohol | 2-ethyl-4-(2,2,3-trimethyl-3-cyclopenten-1-yl)-2-buten-1-ol | 208 |
| benzaldehyde | aromatic aldehyde | benzaldehyde | 106 |
| benzophenone | aromatic ketone | benzophenone | 182 |
| benzyl acetate | ester | benzyl acetate | 150 |
| benzyl salicylate | ester | benzyl salicylate | 228 |
| beta damascone | aliphatic ketone | 1-(2,6,6-trimethyl-1-cyclo-hexen-1-yl)-2-buten-1-one | 192 |
| beta gamma hexanol | alcohol | 3-hexen-1-ol | 100 |
| buccoxime | aliphatic ketone | 1,5-dimethyl-oxime bicyclo[3,2,1] octan-8-one | 167 |
| cedrol | alcohol | octahydro-3,6,8,8-tetramethyl-1H-3A,7-methanoazulen-6-ol | 222 |

-continued

| Common Name | Chemical Type | Chemical Name | Approx. M.W. |
|---|---|---|---|
| cetalox | ether | dodecahydro-3A,6,6,9A-tetramethylnaphtho[2,1B]-furan | 236 |
| cis-3-hexenyl acetate | ester | cis-3-hexenyl acetate | 142 |
| cis-3-hexenyl salicylate | ester | beta, gamma-hexenyl salicylate | 220 |
| citronellol | alcohol | 3,7-dimethyl-6-octenol | 156 |
| citronellyl nitrile | nitrile | geranyl nitrile | 151 |
| clove stem oil | natural | | |
| coumarin | lactone | coumarin | 146 |
| cyclohexyl salicylate | ester | cyclohexyl salicylate | 220 |
| cymal | aromatic aldehyde | 2-methyl-3-(para iso propyl phenyl)propionaldehyde | 190 |
| decyl aldehyde | aliphatic aldehyde | decyl aldehyde | 156 |
| delta damascone | aliphatic ketone | 1-(2,6,6-trimethyl-3-cyclo-hexen-1-yl)-2-buten-1-one | 192 |
| dihydromyrcenol | alcohol | 3-methylene-7-methyl octan-7-ol | 156 |
| dimethyl benzyl carbinyl acetate | ester | dimethyl benzyl carbinyl acetate | 192 |
| ethyl vanillin | aromatic aldehyde | ethyl vanillin | 166 |
| ethyl-2-methyl butyrate | ester | ethyl-2-methyl butyrate | 130 |
| ethylene brassylate | macrocyclic lactone | ethylene tridecan-1,13-dioate | 270 |
| eucalyptol | aliphatic epoxide | 1,8-epoxy-para-menthane | 154 |
| eugenol | alcohol | 4-allyl-2-methoxy phenol | 164 |
| exaltolide | macrocyclic lactone | cyclopentadecanolide | 240 |
| flor acetate | ester | dihydro-nor-cyclopentadienyl acetate | 190 |
| florhydral | aromatic aldehyde | 3-(3-isopropylphenyl)butanal | 190 |
| frutene | ester | dihydro-nor-cyclopentadienyl propionate | 206 |
| galaxolide | ether | 1,3,4,6,7,8-hexahydro-4,6,6,7,8,8-hexamethylcyclopenta-gamma-2-benzopyrane | 258 |
| gamma decalactone | lactone | 4-N-hepty-4-hydroxybutanoic acid lactone | 170 |
| gamma dodecalactone | lactone | 4-N-octyl-4-hydroxy-butanoic acid lactone | 198 |
| geraniol | alcohol | 3,7-dimethyl-2,6-octadien-1-ol | 154 |
| geranyl acetate | ester | 3,7-dimethyl-2,6-octadien-1-yl acetate | 196 |
| geranyl nitrile | ester | 3,7-diemthyl-2,6-octadienenitrile | 149 |
| helional | aromatic aldehyde | alpha-methyl-3,4,(methylenedioxy) hydrocinnamaldehyde | 192 |
| heliotropin | aromatic aldehyde | heliotropin | 150 |
| hexyl acetate | ester | hexyl acteate | 144 |
| hexyl cinnamic aldehyde | aromatic aldehyde | alpha-n-hexyl cinnamic aldehyde | 216 |
| hexyl salicylate | ester | hexyl salicylate | 222 |
| hydroxyambran | aliphatic alcohol | 2-cyclododecyl-propanol | 226 |
| hydroxycitronellal | aliphatic aldehyde | hydroxycitronellal | 172 |
| ionone alpha | aliphatic ketone | 4-(2,6,6-trimethyl-1-cyclohexenyl-1-yl)-3-buten-2-one | 192 |
| ionone beta | aliphatic ketone | 4-(2,6,6-trimethyl-1-cyclohexen-1-yl)-3-butene-2-one | 192 |
| ionone gamma methyl | aliphatic ketone | 4-(2,6,6-trimethyl-2-cyclohexyl-1-yl)-3-methyl-3-buten-2-one | 206 |
| iso E super | aliphatic ketone | 7-acetyl-1,2,3,4,5,6,7,8-octahydro-1,1,6,7,tetramethyl naphthalene | 234 |
| iso eugenol | ether | 2-methoxy-4-(1-propenyl)phenol | 164 |
| iso jasmone | aliphatic ketone | 2-methyl-3-(2-pentenyl)-2-cyclopenten-1-one | 166 |
| koavone | aliphatic aldehyde | acetyl di-isoamylene | 182 |
| lauric aldehyde | aliphatic aldehyde | lauric aldehyde | 184 |
| lavandin | natural | | |
| lavender | natural | | |
| lemon CP | natural | major component d-limonene | |
| d-limonene/orange terpenes | alkene | 1-methyl-4-iso-propyl-1-cyclohexene | 136 |
| linalool | alcohol | 3-hydroxy-3,7-dimethyl-1,6-octadiene | 154 |
| linalyl acetate | ester | 3-hydroxy-3,7-dimethyl-1,6-octadiene acetate | 196 |
| lrg 201 | ester | 2,4-dihydroxy-3,6-dimethyl benzoic acid methyl ester | 196 |

| Common Name | Chemical Type | Chemical Name | Approx. M.W. |
|---|---|---|---|
| lyral | aliphatic aldehyde | 4-(4-hydroxy-4-methyl-pentyl) 3-cylcohexene-1-carboxaldehyde | 210 |
| majantol | aliphatic alcohol | 2,2-dimethyl-3-(3-methylphenyl)-propanol | 178 |
| mayol | alcohol | 4-(1-methylethyl) cyclohexane methanol | 156 |
| methyl anthranilate | aromatic amine | methyl-2-aminobenzoate | 151 |
| methyl beta naphthyl ketone | aromatic ketone | methyl beta naphthyl ketone | 170 |
| methyl cedrylone | aliphatic ketone | methyl cedrenyl ketone | 246 |
| methyl chavicol | ester | 1-methyloxy-4,2-propen-1-yl benzene | 148 |
| methyl dihydro jasmonate | aliphatic ketone | methyl dihydro jasmonate | 226 |
| methyl nonyl acetaldehyde | aliphatic aldehyde | methyl nonyl acetaldehyde | 184 |
| musk indanone | aromatic ketone | 4-acetyl-6-tert butyl-1,1-dimethyl indane | 244 |
| nerol | alcohol | 2-cis-3,7-dimethyl-2,6-octadien-1-ol | 154 |
| nonalactone | lactone | 4-hydroxynonanoic acid, lactone | 156 |
| norlimbanol | aliphatic alcohol | 1-(2,2,6-trimethyl-cyclohexyl)-3-hexanol | 226 |
| orange CP | natural | major component d-limonene | |
| P. T. bucinal | aromatic aldehyde | 2-methyl-3(para tert butylphenyl) propionaldehyde | 204 |
| para hydroxy phenyl butanone | aromatic ketone | para hydroxy phenyl butanone | 164 |
| patchouli | natural | | |
| phenyl acetaldehyde | aromatic aldehyde | 1-oxo-2-phenylethane | 120 |
| phenyl acetaldehyde dimethyl acetal | aromatic aldehyde | phenyl acetaldehyde dimethyl acetal | 166 |
| phenyl ethyl acetate | ester | phenyl ethyl acetate | 164 |
| phenyl ethyl alcohol | alcohol | phenyl ethyl alcohol | 122 |
| phenyl ethyl phenyl acetate | ester | 2-phenylethyl phenyl acetate | 240 |
| phenyl hexanol/phenoxanol | alcohol | 3-methyl-5-phenylpentanol | 178 |
| polysantol | aliphatic alcohol | 3,3-dimethyl-5-(2,2,3-trimethyl-3-cyclopenten-1-yl)-4-penten-2-ol | 221 |
| prenyl acetate | ester | 2-methylbuten-2-ol-4-acetate | 128 |
| rosaphen | aromatic alcohol | 2-methyl-5-phenyl pentanol | 178 |
| sandalwood | natural | | |
| alpha-terpinene | aliphatic alkane | 1-methyl-4-iso-propylcyclohexadiene-1,3 | 136 |
| terpineol (alpha terpineol and beta terpineol) | alcohol | para-menth-1-en-8-ol, para-menth-1-en-1-ol | 154 |
| terpinyl acetate | ester | para-menth-1-en-8-yl acetate | 196 |
| tetra hydro linalool | aliphtic alcohol | 3,7-dimethyl-3-octanol | 158 |
| tetrahydromyrcenol | aliphatic alcohol | 2,6-dimethyl-2-octanol | 158 |
| tonalid/musk plus | aromatic ketone | 7-acetyl-1,1,3,4,4,6-hexamethyl tetralin | 258 |
| undecalactone | lactone | 4-N-heptyl-4-hydroxybutanoic acid lactone | 184 |
| undecaveriol | alcohol | 4-methyl-3-decen-5-ol | 170 |
| undecyl aldehyde | aliphatic aldehyde | undecanal | 170 |
| undecylenic | aliphatic aldehyde | undecylenic aldehyde | 168 |
| vanillin | aromatic aldehyde | 4-hydroxy-3-methoxybenzaldehyde | 152 |
| verdox | ester | 2-tert-butyl cyclohexyl acetate | 198 |
| vertenex | ester | 4-tert-butyl cyclohexyl acetate | 198 | and mixtures thereof.

When high initial perfume odor impact on fabrics is desired, it is also preferable to select a perfume containing perfume ingredients which are not too hydrophobic. The less hydrophobic perfume ingredients are more soluble in water, and are more available in the freshening composition. The degree of hydrophobicity of a perfume ingredient can be correlated with its octanol/water partitioning coefficient P. The octanol/water partitioning coefficient of a perfume ingredient is the ratio between its equilibrium concentration in octanol and in water. A perfume ingredient with a greater partitioning coefficient P is more hydrophobic. Conversely, a perfume ingredient with a smaller partitioning coefficient P is more hydrophilic. The preferred perfume ingredients of this invention have an octanol/water partitioning coefficient P of about 1,000 or smaller. Since the partitioning coefficients of the perfume ingredients normally have high values, they are more conveniently given in the form of their logarithm to the base 10, logP. Thus the perfume ingredients of this invention have logP of about 3 or smaller.

The logP of many perfume ingredients has been reported; for example, the Pomona92 database, available from Daylight Chemical Information Systems, Inc. (Daylog CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990, incorporated herein by reference). The fragment approach is based on the chemical structure of each perfume ingredient, and takes into account the numbers and types of atoms, the atom connectivity, and chemical bonding. The ClogP values, which are the most reliable and widely used estimates for this physicochemical property, are used instead of the experimental logP values in the selection of perfume ingredients which are useful in the present invention.

Non-limiting examples of perfume ingredients which have ClogP values of about 3 or smaller are benzaldehyde, benzyl acetate, cis-3-hexenyl acetate, coumarin, dihydromyrcenol, dimethyl benzyl carbinyl acetate, ethyl vanillin, eucalyptol, eugenol, iso eugenol, flor acetate, geraniol, hydroxycitronellal, koavone, linalool, methyl anthranilate, methyl beta naphthyl ketone, methyl dihydro jasmonate, nerol, nonalactone, phenyl ethyl acetate, phenyl ethyl alcohol, alpha terpineol, beta terpineol, vanillin, and mixtures thereof.

When hydrophilic perfume is desired, at least about 25% by weight of the perfume, more preferably about 50%, most preferably about 75%, is composed of perfume ingredients having a ClogP of about 3 or smaller.

Preferably the freshening composition contains an effective amount of perfume to provide the freshening fragrance to fabrics when first sprayed, some lingering fragrance in-wear, and some extra fragrance to be released upon fabric rewetting. Effective level of perfume is from about 0.01% to about 1%, more preferably from about 0.01% to about 0.5%, most preferably from about 0.015% to about 0.3%, by weight of the composition. The perfume to cyclodextrin weight ratio is typically from about 3:100 to about 100:100, preferably from about 4:100 to about 50:100, more preferably from about 5:100 to about 25:100.

(C). Cyclodextrin

Optionally, but preferably, solubilized, highly water-soluble, cyclodextrin can be added to the composition of the present invention. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. The unique shape and physical-chemical property of the cavity enable the cyclodextrin molecules to absorb (form inclusion complexes with) organic molecules or parts of organic molecules which can fit into the cavity. Many perfume molecules can fit into the cavity.

Non-derivatised (normal) beta-cyclodextrin can be used although it is not preferred due to its low solubility. When non-derivatised beta-cyclodextrin is used, the aqueous solution becomes cloudy and is not clear, as preferred by the present invention. Not to be limited by theory, it is believed that some beta-cyclodextrin and/or beta-cyclodextrin/perfume complexes solidify and/or precipitate out producing an undesirable cloudy aqueous solution.

Preferably, the odor absorbing solution of the present invention is clear. The term "clear" as defined herein means transparent or translucent, preferably transparent as in "water clear," when observed through a layer having a thickness of less than about 10 cm.

Preferably, the cyclodextrins used in the present invention are highly water-soluble such as, alpha-cyclodextrin and derivatives thereof, gamma-cyclodextrin and derivatives thereof, derivatised beta-cyclodextrins, and/or mixtures thereof. The derivatives of cyclodextrin consist mainly of molecules wherein some of the OH groups are converted to OR groups. Cyclodextrin derivatives include, e.g., those with short chain alkyl groups such as methylated cyclodextrins, and ethylated cyclodextrins, wherein R is a methyl or an ethyl group; those with hydroxyalkyl substituted groups, such as hydroxypropyl cyclodextrins and/or hydroxyethyl cyclodextrins, wherein R is a $-CH_2-CH(OH)-CH_3$ or a $-CH_2CH_2-OH$ group; branched cyclodextrins such as maltose-bonded cyclodextrins; cationic cyclodextrins such as those containing 2-hydroxy-3(dimethylamino)propyl ether, wherein R is $CH_2-CH(OH)-CH_2-N(CH_3)_2$ which is cationic at low pH; quaternary ammonium, e.g., 2-hydroxy-3-(trimethylammonio)propyl ether chloride groups, wherein R is $CH_2-CH(OH)-CH_2-N^+(CH_3)_3Cl^-$; anionic cyclodextrins such as carboxymethyl cyclodextrins, cyclodextrin sulfates, and cyclodextrin succinylates; amphoteric cyclodextrins such as carboxymethyl/quaternary ammonium cyclodextrins; cyclodextrins wherein at least one glucopyranose unit has a 3-6-anhydro-cyclomalto structure, e.g., the mono-3-6-anhydrocyclodextrins, as disclosed in "Optimal Performances with Minimal Chemical Modification of Cyclodextrins", F. Diedaini-Pilard and B. Perly, The 7th International Cyclodextrin Symposium Abstracts, Apr. 1994, p. 49, herein incorporated by reference; and mixtures thereof. Other cyclodextrin derivatives are disclosed in U.S. Pat. No. 3,426,011, Parmerter et al., issued Feb. 4, 1969; U.S. Pat. Nos. 3,453,257; 3,453,258; 3,453,259; and 3,453,260, all in the names of Parmerter et al., and all issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565,887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,678,598, Ogino et al., issued Jul. 7, 1987; U.S. Pat. No. 4,638,058, Brandt et al., issued Jan. 20, 1987; and U.S. Pat. No. 4,746,734, Tsuchiyama et al., issued May 24, 1988; all of said patents being incorporated herein by reference.

Highly water-soluble cyclodextrins are those having water solubility of at least about 10 g in 100 ml of water at room temperature, preferably at least about 20 g in 100 ml of water, more preferably at least about 25 g in 100 ml of water at room temperature. Examples of preferred water-soluble cyclodextrin derivatives suitable for use herein are hydroxypropyl alpha-cyclodextrin, methylareal alpha-cyclodextrin, methylated beta-cyclodextrin, hydroxyethyl beta-cyclodextrin, and hydroxypropyl beta-cyclodextrin. Hydroxyalkyl cyclodextrin derivatives preferably have a degree of substitution of from about 1 to about 14, more preferably from about 1.5 to about 7, wherein the total number of OR groups per cyclodextrin is defined as the degree of substitution. Methylated cyclodextrin derivatives typically have a degree of substitution of from about 1 to about 18, preferably from about 3 to about 16. A known methylated beta-cyclodextrin is heptakis-2,6-di-O-methyl- β-cyclodextrin, commonly known as DIMEB, in which each glucose unit has about 2 methyl groups with a degree of substitution of about 14. A preferred, more commercially available methylated beta-cyclodextrin is a randomly methylated beta-cyclodextrin having a degree of substitution of about 12.6. The preferred cyclodextrins are available, e.g., from American Maize-Products Company and Wacker Chemicals (USA), Inc.

It is also preferable to use a mixture of cyclodextrins. Such mixtures can complex with a wider range of perfume molecules having a wider range of molecular sizes. Preferably at least a portion of the cyclodextrins is alpha-cyclodextrin and its derivatives thereof, gamma-cyclodextrin and its derivatives thereof, and/or derivatised beta-cyclodextrin, and mixtures thereof.

Cyclodextrin molecules are known for their ability to form complexes with perfume ingredients and have typically been taught as a perfume carrier. The prior art teaches the use of drier-added fabric softener sheets containing high levels of cyclodextrin/perfume complexes wherein the fabrics treated with this solid cyclodextrin complex release perfume when the fabrics are rewetted. The art also teaches that cyclodextrin/perfume complexes used in aqueous rinse-added fabric softener compositions must be protected, e.g., with a hydrophobic wax coating so the cyclodextrin/perfume complexes will not decompose due to the presence of water. See U.S. Pat. No. 5,102,564 Gardlik et al., issued Apr.7, 1992; U.S. Pat. No. 5,234,610, Gardlik et al., issued Aug. 10, 1993; U.S. Pat. No. 5,234,611 Trinh, et al., issued Aug. 10, 1993, all of said patents incorporated herein by reference. It is therefore highly surprising and unexpected to find that fabrics treated with the aqueous compositions of the present invention, which contain low levels of unprotected cyclodextrin, also exhibit perfume release upon rewetting. This phenomenon provides a benefit in that fabrics treated with the composition of the present invention will thus remain fresh longer, via a perfume release, when said fabrics are rewetted, such as when the wearer perspires.

For reducing malodor impression on fabrics, the composition is preferably used as a spray. It is preferable that the composition of the present invention contain low levels of cyclodextrin so that a visible stain does not appear on the fabric at normal usage levels. Preferably, the solution is not discernible when dry. Typical levels of cyclodextrin are from about 0.1% to about 5%, preferably from about 0.2% to about 4%, more preferably from about 0.3% to about 3%, most preferably from about 0.4% to about 2%, by weight of the composition. Compositions with higher concentrations can leave unacceptable visible stains on fabrics as the solution evaporates off of the fabric. This is especially a problem on thin, colored, synthetic fabrics. In order to avoid or minimize the occurrence of fabric staining, it is preferable that the fabric be treated at a level of less than about 5 mg of cyclodextrin per mg of fabric, more preferably less than about 2 mg of cyclodextrin per mg of fabric.

Concentrated compositions can also be used in order to provide a less expensive product. When a concentration is used, i.e., when the level of cyclodextrin used is from about 3% to about 5%, it is preferable to dilute the composition before treating fabrics in order to avoid staining. Preferably the cyclodextrin is diluted with about 50% to about 2000%, more preferably with about 60% to about 1000%, most preferably with about 75% to about 500%, by weight of the composition, of water.

(D). Solubilizing Aid

The composition of the present invention can also optionally contain a solubilizing aid to solubilize any excess hydrophobic organic materials, e.g., perfume, insect repelling agent, antioxidant, etc., that are not readily soluble in the composition, to form a clear solution. A suitable solubilizing aid is surfactant, preferably no-foaming or low-foaming surfactant. Suitable surfactants are nonionic surfactants, anionic surfactants, cationic surfactants, amphoteric surfactants, zwitterionic surfactants, and mixtures thereof. Suitable surfactants can be emulsifiers and/or detersive surfactants. Mixtures of emulsifiers and detersive surfactants are also preferred. When a surfactant containing one, or more, aliphatic alkyl group is used, it is preferred that it contain relatively short alkyl chains of from about 5 to about 14 carbon atoms. Preferred nonionic surfactants are polyethylene glycol-polypropylene glycol block copolymers, such as Pluronic® and Plutonic R® surfactants from BASF; Tetronic® and Tetronic R® surfactants from BASF, ethoxylated branched aliphatic diols such as Surfynol® surfactants from Air Products; ethoxylated alkyl phenols, such as Igepal® surfactants from Rhône-Poulenc; ethoxylated aliphatic alcohols and carboxylic acids; polyethylene glycol diesters of fatty acids; fatty acid esters of ethoxylated sorbitans; and mixtures thereof. Preferred anionic surfactants are dialkyl sulfosuccinate, alkylarylsulfonate, fatty alcohol sulfate, paraffin sulfonate, alkyl sarcosinate, alkyl isethionate salts having suitable cations, e.g., sodium, potassium, alkanol ammonium, etc., and mixtures thereof. Preferred amphoteric surfactants are the betaines. It is preferred that the surfactant have good wetting properties. Also preferred are surfactants that have the hydrophilic groups situated between hydrophobic chains, such as Pluronic R® surfactants, Surfynol surfactants, polyethylene glycol diesters of fatty acids, fatty acid esters of ethoxylated sorbitans, dialkyl sulfosuccinate, di($C_8$-$C_{12}$ alkyl)di(C1-C2 alkyl)ammonium halides, and mixtures thereof; or surfactants that have the hydrophobic chains situated between hydrophilic groups, such as Pluronic surfactants; and mixtures thereof. Mixtures of these surfactants and other types of surfactants are also preferred to form no-foaming or low-foaming solubilizing agents. Polyalkylene glycol can be used as a defoaming agent in combination with the solubilizing agents.

If solubilizing agent is used in the present compositions, it is typically used at a level of from about 0.05% to about 1% by weight of the composition, more preferably from about 0.05% to about 0.3%, most preferably from about 0.1% to about 0.3%, by weight of the composition.

(E). Carrier

Aqueous solutions are preferred in the present invention for the reduction of malodor impression. The preferred aqueous carrier of the present invention is water. The water which is used can be distilled, deionized, or tap water. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the composition of the present invention due to the addition of these alcohols to such things as perfumes and as stabilizers for some preservatives, it is preferably that the level of monohydric alcohol be less than about 5%, preferably less than about 3%, more preferably less than about 1%, by weight of the composition.

It has recently been discovered that water has an unexpected odor controlling effect of its own. It has been discovered that the intensity of the odor generated by some polar, low molecular weight organic amines, acids, and mercaptans is reduced when the odor-contaminated fabrics are treated with an aqueous solution. Not to be bound by theory, it is believed that water solubilizes and depresses the vapor pressure of these polar, low molecular weight organic molecules, thus reducing their odor intensity.

(E). Other Optional Ingredients

Adjuvants can be optionally added to the fabric freshening composition herein for their known purposes. Such adjuvants include, but are not limited to, preservatives, bacteriocides, fungicides, water-soluble polymers, antistatic agents, insect and moth repelling agents, colorants, especially bluing agents, antioxidants, and mixtures thereof.

(1). Preservative

The composition of the present invention can optionally contain solubilized, water-soluble, antimicrobial preservative, especially when cyclodextrin is added to the composition because cyclodextrin molecules are made up of varying numbers of glucose units which can make them a prime breeding ground for certain microorganisms, especially when in aqueous compositions. This drawback can lead to the problem of storage stability of cyclodextrin solutions for any significant length of time. Contamination by certain microorganisms with subsequent microbial growth resulting in an unsightly and/or malodorous solution. Because microbial growth in cyclodextrin solutions is highly objectionable when it occurs, it is preferable to include a water-soluble, antimicrobial preservative, which is effective for inhibiting and/or regulating microbial growth in order to increase storage stability of the preferably clear, aqueous odor-absorbing solution containing water-soluble cyclodextrin.

Typical microorganisms that can be found in cyclodextrin supplies and whose growth are found to be enhanced by the presence of cyclodextrin in aqueous cyclodextrin solutions include bacteria, e.g., *Bacillus thuringiensis* (cereus group) and *Bacillus sphaeficus;* fungi, e.g., *Aspergillus ustus. Bacillus sphaericus* is one of the most numerous members of Bacillus species in soils. *Aspergillus ustus* is common in grains and flours which are raw materials to produce cyclodextrins. Microorganisms such as *Escherichia coli* and *Pseudomonas aeruginosa* are found in some water sources, and can be introduced during the preparation of cyclodextrin aqueous solutions.

It is preferable to use a broad spectrum preservative, e.g., one that is effective on both bacteria (both gram positive and gram negative) and fungi. A limited spectrum preservative, e.g., one that is only effective on a single group of microorganisms, e.g., fungi, can be used in combination with a broad spectrum preservative or other limited spectrum preservatives, with complimentary activity. A mixture of broad spectrum preservatives can also be used.

Antimicrobial preservatives useful in the present invention can be biocidal compounds, i.e., substances that kill microorganisms, or biosratio compounds, i.e., substances that inhibit and/or regulate the growth of microorganisms.

Preferred antimicrobial preservatives are those that are water-soluble and are effective at low levels because the organic preservatives can form inclusion complexes with the cyclodextrin molecules and compete with the perfume molecules for the cyclodextrin cavities, thus rendering the cyclodextrins ineffective as freshening actives. Water-soluble preservatives useful in the present invention are those that have a solubility in water of at least about 0.3 g per 100 ml of water, i.e., about 0.3% at room temperature, preferably greater than about 0.5% at room temperature. These types of preservatives have a lower affinity to the cyclodextrin cavity, at least in the aqueous phase, and are therefore more available to provide antimicrobial activity. Preservatives with a water-solubility of less than about 0.3% and a molecular structure that readily fits into the cyclodextrin cavity, have a greater tendency to form inclusion complexes with the cyclodextrin molecules, thus rendering the preservative less effective to control microbes in the cyclodextrin solution. Therefore, many well known preservatives such as short chain alkyl esters of p-hydroxybenzoic acid, commonly known as parabens; N-(4-chlorophenyl)-N'-(3,4-dichlorophenyl) urea, also known as 3,4,4'-trichlorocarbanilide or triclocarban; 2,4,4'-trichloro-2'-hydroxy diphenyl ether, commonly known as triclosan are not preferred in the present invention since they are relatively ineffective when used in conjunction with cyclodextrin.

The water-soluble antimicrobial preservative is included in the present invention it is included at an effective amount. The term "effective amount" as herein defined means a level sufficient to prevent spoilage or prevent growth of inadvertently added microorganisms for a specific period of time, but not sufficient enough to contribute to the odor absorbing performance of the composition. In other words, the preservative is not being used to kill microorganisms on the surface onto which the composition is deposited in order to eliminate odors produced by microorganisms. Instead, it is preferably being used to prevent spoilage of the cyclodextrin solution in order to increase the shelf-life of the composition. Preferred levels of preservative are from about 0.0001% to about 0.3%, more preferably from about 0.0002% to about 0.2%, most preferably from about 0.0003% to about 0.1%, by weight of the composition.

The preservative can be an organic material, which will not cause damage to fabric appearance, e.g., discoloration, coloration, bleaching. Preferred water-soluble preservatives include organic sulfur compounds, halogenated compounds, cyclic organic nitrogen compounds, low molecular weight aldehydes, quaternary compounds, dehydroacetic acid, phenyl and phenoxy compounds, and mixtures thereof.

The following are non-limiting examples of preferred water-soluble preservatives for use in the present invention.

(a). Organic Sulfur Compounds

Preferred water-soluble preservatives for use in the present invention are organic sulfur compounds. Some non-limiting examples of organic sulfur compounds suitable for use in the present invention are:

(i). 3-Isothiazolone Compounds

A preferred preservative is an antimicrobial, organic preservative containing 3-isothiazolone groups having the formula:

$$\begin{array}{c} R^1 \\ \diagup\!\!\!\!\diagdown \\ R^2 \end{array} \!\!\!\!= \!\!\!\! \begin{array}{c} O \\ \| \\ C \\ | \\ N-Y \\ | \\ S \end{array}$$

wherein

Y is an unsubstituted alkyl, alkenyl, or alkynyl group of from about 1 to about 18 carbon atoms, an unsubstituted or substituted cycloalkyl group having from about a 3 to about a 6 carbon ring and up to 12 carbon atoms, an unsubstituted or substituted aralkyl group of up to about 10 carbon atoms, or an unsubstituted or substituted aryl group of up to about 10 carbon atoms;

$R^1$ is hydrogen, halogen, or a ($C_1$-$C_4$) alkyl group; and $R^2$ is hydrogen, halogen, or a ($C_1$-$C_4$) alkyl group.

Preferably, when Y is methyl or ethyl, $R^1$ and $R^2$ should not both be hydrogen. Salts of these compounds formed by reacting the compound with acids such as hydrochloric, nitric, sulfuric, etc. are also suitable.

This class of compounds is disclosed in U.S. Pat. No. 4,265,899, Lewis et al., issued May 5, 1981, and incorporated herein by reference. Examples of said compounds are: 5-chloro-2-methyl-4-isothiazolin-3-one; 2-n-butyl-3-isothiazolone; 2-benzyl-3-isothiazolone; 2-phenyl-3-isothiazolone, 2-methyl-4,5-dichloroisothiazolone; 5-chloro-2-methyl-3-isothiazolone; 2-methyl-4-isothiazolin-3-one; and mixtures thereof. A preferred preservative is a water-soluble mixture of 5-chloro-2-methyl-4-isothiazolin-3-one and 2-methyl-4-isothiazolin-3-one, more preferably a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Company.

When Kathon® is used as the preservative in the present invention it is typically present at a level of from about 0.0001% to about 0.01%, preferably from about 0.0002% to about 0.005%, more preferably from about 0.0003% to about 0.003%, most preferably from about 0.0004% to about 0.002%, by weight of the composition.

(ii). Sodium Pyrithione

Another preferred organic sulfur preservative is sodium pyrithione, with water solubility of about 50%. When sodium pyrithione is used as the preservative in the present invention it is typically present at a level of from about 0.0001% to about 0.01%, preferably from about 0.0002% to about 0.005%, more preferably from about 0.0003% to about 0.003%, by weight of the composition.

Mixtures of the preferred organic sulfur compounds can also be used as the preservative in the present invention.

(b). Halogenated Compounds

Preferred preservatives for use in the present invention are halogenated compounds. Some non-limiting examples of halogenated compounds suitable for use in the present invention are:

5-bromo-5-nitro-1,3-dioxane, available under the trade name Bronidox L® from Henkel. Bronidox L® has a solubility of about 0.46% in water. When Bronidox is used as the preservative in the present invention it is typically present at a level of from about 0.0005% to about 0.02%, preferably from about 0.001% to about 0.01%, by weight of the composition;

2-bromo-2-nitropropane-1,3-diol, available under the trade name Bronopol from Inolex can be used as the preservative in the present invention. Bronopol has a solubility of about 25% in water. When Bronopol is used as the preservative in the present invention it is typically present at a level of from about 0.002% to about 0.1%, preferably from about 0.005% to about 0.05%, by weight of the composition;

1,1'-hexamethylene bis(5-(p-chlorophenyl)biguanide), commonly known as chlorhexidine, and its salts, e.g., with acetic and gluconic acids can be used as a preservative in the present invention. The digluconate salt is highly water-soluble, about 70% in water, and the diacetate salt has a solubility of about 1.8% in water. When chlorohexidine is used as the preservative in the present invention it is typically present at a level of from about 0.0001% to about 0.04%, preferably from about 0.0005% to about 0.01%, by weight of the composition.

1,1,1-Trichloro-2-methylpropan-2-ol, commonly known as chlorobutanol, with water solubility of about 0.8%; a typical effective level of chlorobutanol is from about 0.1% to about 0.5%, by weight of the composition.

4,4'-(Trimethylenedioxy)bis-(3-bromobenzamidine)diisethionate, or dibromopropamidine, with water solubility of about 50%; when dibromopropamidine is used as the preservative in the present invention it is typically present at a level of from about 0.0001% to about 0.05%, preferably from about 0.0005% to about 0.01% by weight of the composition.

Mixtures of the preferred halogenated compounds can also be used as the preservative in the present invention.

(c). Cyclic Organic Nitrogen Compounds

Preferred water-soluble preservatives for use in the present invention are cyclic organic nitrogen compounds. Some non-limiting examples of cyclic organic nitrogen compounds suitable for use in the present invention are:

(i). Imidazolidinedione Compounds

Preferred preservatives for use in the present invention are imidazolidione compounds. Some non-limiting examples of imidazolidinedione compounds suitable for use in the present invention are:

1,3-bis(hydroxymethyl)-5,5-dimethyl-2,4-imidazolidinedione, commonly known as dimethyloldimethylhydantoin, or DMDM hydantoin, available as, e.g., Glydant® from Lonza. DMDM hydantoin has a water solubility of more than 50% in water, and is mainly effective on bacteria. When DMDM hydantoin is used, it is preferable that it be used in combination with a broad spectrum preservative such as Kathon CG®, or formaldehyde. A preferred mixture is about a 95:5 DMDM hydantoin to 3-butyl-2-iodopropynylcarbamate mixture, available under the trade name Glydant Plus® from Lonza. When Glydant Plus® is used as the preservative in the present invention, it is typically present at a level of from about 0.005% to about 0.2%;

N-[1,3-bis(hydroxymethyl)2,5-dioxo-4-imidazolidinyl]-N,N'-bis(hydroxymethyl) urea, commonly known as diazolidinyl urea, available under the trade name Germall II® from Sutton Laboratories, Inc. (Sutton) can be used as the preservative in the present invention. When Germall II® is used as the preservative in the present invention, it is typically present at a level of from about 0.01% to about 0.1%;

N,N"-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from (Sutton) can be used as the preservative in the present invention. When imidazolidinyl urea is used as the preservative, it is typically present at a level of from about 0.05% to about 0.2%, by weight of the composition.

Mixtures of the preferred imidazolidinedione compounds can also be used as the preservative in the present invention.

(ii). Polymethoxy Bicyclic Oxazolidine

Another preferred water-soluble cyclic organic nitrogen preservative is polymethoxy bicyclic oxazolidine, having the general formula:

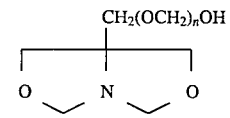

where n has a value of from about 0 to about 5, and is available under the trade name Nuosept® C from Hills America. When Nuosept® C is used as the preservative, it is typically present at a level of from about 0.005% to about 0.1%, by weight of the composition.

Mixtures of the preferred cyclic organic nitrogen compounds can also be used as the preservative in the present invention.

(d). Low Molecular Weight Aldehydes (i). Formaldehyde

A preferred preservative for use in the present invention is formaldehyde. Formaldehyde is a broad spectrum preservative which is normally available as formalin which is a 37% aqueous solution of formaldehyde. When formaldehyde is used as the preservative in the present invention, typical levels are from about 0.003% to about 0.2%, preferably from about 0.008% to about 0.1%. more preferably from about 0.01% to about 0.05%, by weight of the composition.

(ii). Glutaraldehyde

A preferred preservative for use in the present invention is glutaraldehyde. Glutaraldehyde is a water-soluble, broad spectrum preservative commonly available as a 25% or a 50% solution in water. When glutaraldehyde is used as the preservative in the present invention it is typically present at a level of from about 0.005% to about 0.1%, preferably from about 0.01% to about 0.05%, by weight of the composition.

(e). Quaternary Compounds

Preferred preservatives for use in the present invention are cationic and/or quaternary compounds. Such compounds include polyaminopropyl biguanide, also known as polyhexamethylene biguanide having the general formula:

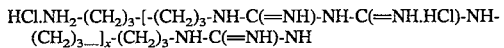

Polyaminopropyl biguanide is a water-soluble, broad spectrum preservative which is available as a 20% aqueous solution available under the trade name Cosmocil CQ® from ICI Americas, Inc., or under the trade name Mikrokill® from Brooks, Inc.

1-(3-Chlorallyl)-3,5,7-triaza-1-azoniaadamantane chloride, available, e.g., under the trade name Dowicil 200 from Dow Chemical, is an effective quaternary ammonium preservative; it is freely soluble in water; however, it has the tendency to discolor (yellow), therefore it is not highly preferred.

Mixtures of the preferred quaternary ammonium compounds can also be used as the preservative in the present invention.

When quaternary ammonium compounds are used as the preservative in the present invention, they are typically present at a level of from about 0.005% to about 0.2%, preferably from about 0.01% to about 0.1%, by weight of the composition.

(f). Dehydroacetic Acid

A preferred preservative for use in the present invention is dehydroacetic acid. Dehydroacetic acid is a broad spectrum preservative preferably in the form of a sodium or a potassium salt so that it is water-soluble. This preservative acts more as a biostatic preservative than a biocidal preservative. When dehydroacetic acid is used as the preservative it is typically used at a level of from about 0.005% to about 0.2%, preferably from about 0.008% to about 0.1%, more preferably from about 0.01% to about 0.05%, by weight of the composition.

(g). Phenyl and Phenoxy Compounds

Some non-limiting examples of phenyl and phenoxy compounds suitable for use in the present invention are:

4,4'-diamidino-α,ω-diphenoxypropane diisethionate, commonly known as propamidine isethionate, with water solubility of about 16%; and 4,4'-diamidino-α,ω-diphenoxyhexane diisethionate, commonly known as hexamidine isethionate. Typical effective level of these salts is about 0.0002% to about 0.05%.

Other examples are benzyl alcohol, with a water solubility of about 4%; 2-phenylethanol, with a water solubility of about 2%; and 2-phenoxyethanol, with a water solubility of about 2.67%; typical effective level of these phenyl and phenoxy alcohol is from about 0.1% to about 0.5%, by weight of the composition.

(h). Mixtures thereof

The preservatives of the present invention can be used in mixtures in order to control a broad range of microorganisms.

(2). Water-Soluble Polymers

Some water-soluble polymers, e.g., water-soluble cationic polymer and water-soluble anionic polymers can be used in the composition of the present invention to provide additional odor control benefits.

a. Cationic polymers

Water-soluble cationic polymers, e.g., those containing amino functionalities, amido functionalities, and mixtures thereof, are useful in the present invention to control certain acid-type odors.

b. Anionic polymers

Water-soluble anionic polymers, e.g., polyacrylic acids and their water-soluble salts are useful in the present invention to control certain amine-type odors. Preferred polyacrylic acids and their alkali metal salts have an average molecular weight of less than about 20,000, more preferably less than 5,000. Polymers containing sulfonic acid groups, phosphoric acid groups, phosphonic acid groups, and their water-soluble salts, and mixtures thereof, and mixtures with carboxylic acid and carboxylate groups, are also suitable.

Water-soluble polymers containing both cationic and anionic functionalities are also suitable. Examples of these polymers are given in U.S. Pat. No. 4,909,986, issued Mar. 20, 1990 to N. Kobayashi and A. Kawazoe, incorporated herein by reference. Another example of water-soluble polymers containing both cationic and anionic functionalities is a copolymer of dimethyldiallyl ammonium chloride and acrylic acid, commercially available under the trade name Merquat 280® from Calgon.

(3). Antistatic Agents

The composition of the present invention can optionally contain an effective amount of antistatic agent to provide the treated clothes with in-wear static. Preferred antistatic agents are those that are water soluble in at least effective amount, such that the composition remains a clear solution. Examples of these antistatic agents are monoalkyl cationic quaternary ammonium compounds, e.g., mono($C_{10}$-$C_{14}$ alkyl)trimethyl ammonium halide, such as monolauryl trimethyl ammonium chloride, hydroxycetyl hydroxyethyl dimethyl ammonium chloride, available under the trade name Dehyquart E® from Henkel, and ethyl bis(polyethoxy ethanol) alkylammonium ethylsulfate, available under the trade name. Variquat 66® from Witco Corp., polyethylene glycols, polymeric quaternary ammonium salts, such as polymers conforming to the general formula:

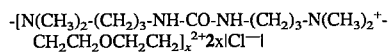

available under the trade name Moirapol A-15® from Rhône-Poulenc, and

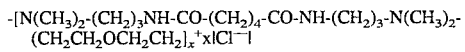
-[N(CH₃)₂-(CH₂)₃NH-CO-(CH₂)₄-CO-NH-(CH₂)₃-N(CH₃)₂-(CH₂CH₂OCH₂CH₂]ₓ⁺xlCl⁻| available under the trade name Mirapol AD-1® from Rhone-Poulenc, quaternized polyethyleneimines, vinylpyrrolidone/methacrylamidopropyltrimethylammonium chloride copolymer, available under the trade name Gafquat HS-100® from GAF; triethonium hydrolyzed collagen ethosulfate, available under the trade name Quat-Pro E® from Maybrook; and mixtures thereof.

It is preferred that a no foaming, or low foaming, agent is used, to avoid foam formation during fabric treatment. It is also preferred that polyethoxylated agents such as polyethylene glycol or Variquat 66® are not used when alpha-cyclodextrin is used. The polyethoxylate groups have a strong affinity to, and readily complex with, alpha-cyclodextrin which in turn depletes the uncomplexed cyclodextrin available for odor control.

When an antistatic agent is used it is typically present at a level of from about 0.05% to about 10%, preferably from about 0.1% to about 5%, more preferably from about 0.3% to about 3%, by weight of the composition.

(4). Insect and/or Moth Repelling Agent

The composition of the present invention can optionally contain an effective amount of insect and/or moth repelling agents. Typical insect and moth repelling agents are pheromones, such as anti-aggregation pheromones, and other natural and/or synthetic ingredients. Preferred insect and moth repellent agents useful in the composition of the present invention are perfume ingredients, such as citronellol, citranellal, citral, linalool, cedar extract, geranium oil, sandalwood oil, 2-(diethylphenoxy)ethanol, 1-dodecene, etc. Other examples of insect and/or moth repellents useful in the composition of the present invention are disclosed in U.S. Pat. Nos. 4,449,987, 4,693,890, 4,696,676, 4,933,371, 5,030,660, 5,196,200, and in "Semio Activity of Flavor and Fragrance Molecules on Various Insect Species", B. D. Mookherjee et al., published in *Bioactive Volatile Compounds from Plants,* ASC Symposium Series 525, R. Teranishi, R. G. Buttery, and H. Sugisawa, 1993, pp. 35–48, all of said patents and publications incorporated herein by reference. When an insect and/or moth repellent is used it is typically present at a level of from about 0.005% to about 3%,, by weight of the composition.

(5). Colorant

Colorants and dyes, especially bluing agents, can be optionally added to the odor absorbing compositions for visual appeal and performance impression. When colorants are used, they are used at extremely low levels to avoid fabric staining. Preferred colorants for use in the present compositions are highly water-soluble dyes, e.g., Liquitint® dyes available from Milliken Chemical Co. Non-limiting examples of suitable dyes are, Liquitint Blue HP®, Liquitint Blue 65®, Liquitint Patent Blue®, Liquitint Royal Blue®, Liquitint Experimental Yellow 8949-43®, Liquitint Green HMC®, Liquitint Yellow II®, and mixtures thereof, preferably Liquitint Blue HP®, Liquitint Blue 65®, Liquitint Patent Blue®, Liquitint Royal Blue®, Liquitint Experimental Yellow 8949-43®, and mixtures thereof (6). Low Molecular Weight Polyols Low molecular weight polyols with relatively high boiling points, as compared to water, such as ethylene glycol, propylene glycol and/or glycerol are preferred optional ingredients for improving odor control performance of the composition of the present invention. Not to be bound by theory, it is believed that the incorporation of a small amount of low molecular weight glycols into the composition of the present invention enhances the formation of the cyclodextrin inclusion complexes as the fabric dries.

It is believed that the polyois ability to remain on the fabric for a longer period of time than water, as the fabric dries, allows them to form ternary complexes with the cyclodextrin and some malodorous molecules. The addition of the glycols is believed to fill up void space in the cyclodextrin cavity that is unable to be filled by some malodor molecules of relatively smaller sizes. Preferably the glycol used is ethylene glycol, and/or propylene glycol. Cyclodextrins prepared by processes that result in a level of such polyols are highly desirable, since they can be used without removal of the polyols.

When glycols are added to the composition of the present invention the preferred weight ratio of low molecular weight polyol to cyclodextrin is from about 1:1,000 to about 20:100, more preferably from about 3:1,000 to about 15:100, even more preferably from about 5:1,000 to about 10:100, and most preferably from about 1:100 to about 7:100.

II. ARTICLE OF MANUFACTURE

The composition of the present invention can also be used in an article of manufacture comprising said composition plus a spray dispenser. When the commercial embodiment of the article of manufacture is used, it is optional, but preferable, to include the preservative. Therefore, the most basic article of manufacture comprises uncomplexed cyclodextrin, a carrier, and a spray dispenser.

Spray Dispenser

The article of manufacture herein comprises a spray dispenser. The composition is placed into a spray dispenser in order to be distributed onto the fabric. Said spray dispenser is any of the manually activated means for producing a spray of liquid droplets as is known in the art, e.g. trigger-type, pump-type, non-aerosol self-pressurized, and aerosol-type spray means. The spray dispenser herein does not include those that will substantially foam the clear, aqueous. It is preferred that at least about 80%, more preferably, at least about 90% of the droplets have a particle size of larger than about 30 µm.

The spray dispenser can be an aerosol dispenser. Said aerosol dispenser comprises a container which can be constructed of any of the conventional materials employed in fabricating aerosol containers. The dispenser must be capable of withstanding internal pressure in the range of from about 20 to about 110 p.s.i.g., more preferably from about 20 to about 70 p.s.i.g. The one important requirement concerning the dispenser is that it be provided with a valve member which will permit the clear, aqueous odor absorbing composition contained in the dispenser to be dispensed in the form of a spray of very fine, or finely divided, particles or droplets. The aerosol dispenser utilizes a pressurized sealed container from which the composition is dispensed through a special actuator/valve assembly under pressure. The aerosol dispenser is pressurized by incorporating therein a gaseous component generally known as a propellant. Common aerosol propellants, e.g., gaseous hydrocarbons such as isobutane, and mixed halogenated hydrocarbons, are not preferred. Halogenated hydrocarbon propellants such as chlorofluoro hydrocarbons have been alleged to contribute to environmental problems. Hydrocarbon propellants can form complexes with the cyclodextrin molecules thereby reducing the availability of uncomplexed cyclodextrin molecules for odor absorption. Preferred propellants are compressed air, nitrogen, inert gases, carbon dioxide, etc. A more complete description of commercially available aerosol-spray dispensers appears in U.S. Pat. No. 3,436,772, Stebbins, issued Apr. 8, 1969; and U.S. Pat. No. 3,600,325, Kaufman et al., issued Aug. 17, 1971; both of said references are incorporated herein by reference.

Preferably the spray dispenser can be a self-pressurized non-aerosol container having a convoluted liner and an elastomeric sleeve. Said self-pressurized dispenser comprises a liner/sleeve assembly containing a thin, flexible radially expandable convoluted plastic liner of from about 0.010 to about 0.020 inch thick, inside an essentially cylindrical elastomeric sleeve. The liner/sleeve is capable of holding a substantial quantity of odor-absorbing fluid product and of causing said product to be dispensed. A more complete description of self-pressurized spray dispensers can be found in U.S. Pat. No. 5,111,971, Winer, issued May 12, 1992, and U.S. Pat. No. 5,232,126, Winer, issued Aug. 3, 1993; both of said references are herein incorporated by reference. Another type of aerosol spray dispenser is one wherein a barrier separates the odor absorbing composition from the propellant (preferably compressed air or nitrogen) and disclosed in U.S. Pat. No. 4,260,110, issued Apr. 7, 1981, and incorporated herein by reference. Such a dispenser is available from EP Spray Systems, East Hanover, N.J.

More preferably, the spray dispenser is a non-aerosol, manually activated, pump-spray dispenser. Said pump-spray dispenser comprises a container and a pump mechanism which securely screws or snaps onto the container. The container comprises a vessel for containing the aqueous odor-absorbing composition to be dispensed.

The pump mechanism comprises a pump chamber of substantially fixed volume, having an opening at the inner end thereof. Within the pump chamber is located a pump stem having a piston on the end thereof disposed for reciprocal motion in the pump chamber. The pump stem has a passageway there through with a dispensing outlet at the outer end of the passageway and an axial inlet port located inwardly thereof.

The container and the pump mechanism can be constructed of any conventional material employed in fabricating pump-spray dispensers, including, but not limited to: polyethylene; polypropylene; polyethyleneterephthalate; blends of polyethylene, vinyl acetate, and rubber elastomer. A preferred container is made of clear, e.g., polyethylene terephthalate. Other materials can include stainless steel. A more complete disclosure of commercially available dispensing devices appears in: U.S. Pat. No. 4,895,279, Schultz, issued Jan. 23, 1990; U.S. Pat. No. 4,735,347, Schultz et al., issued Apr. 5, 1988; and U.S. Pat. No. 4,274,560, Carter, issued Jun. 23, 1981; all of said references are herein incorporated by reference.

Most preferably, the spray dispenser is a manually activated trigger-spray dispenser. Said trigger-spray dispenser comprises a container and a trigger both of which can be constructed of any of the conventional material employed in fabricating trigger-spray dispensers, including, but not limited to: polyethylene; polypropylene; polyacetal; polycarbonate; polyethyleneterephthalate; polyvinyl chloride; polystyrene; blends of polyethylene, vinyl acetate, and rubber elastomer. Other materials can include stainless steel and glass. A preferred container is made of clear, e.g. polyethylene terephthalate. The trigger-spray dispenser does not incorporate a propellant gas into the odor-absorbing composition, and preferably it does not include those that will foam the odor-absorbing composition. The trigger-spray dispenser herein is typically one which acts upon a discrete amount of the odor-absorbing composition itself, typically by means of a piston or a collapsing bellows that displaces the composition through a nozzle to create a spray of thin liquid. Said trigger-spray dispenser typically comprises a pump chamber having either a piston or bellows which is movable through a limited stroke response to the trigger for varying the volume of said pump chamber. This pump chamber or bellows chamber collects and holds the product for dispensing. The trigger spray dispenser typically has an outlet check valve for blocking communication and flow of fluid through the nozzle and is responsive to the pressure inside the chamber. For the piston type trigger sprayers, as the trigger is compressed, it acts on the fluid in the chamber and the spring, increasing the pressure on the fluid. For the bellows spray dispenser, as the bellows is compressed, the pressure increases on the fluid. The increase in fluid pressure in either trigger spray dispenser acts to open the top outlet check valve. The top valve allows the product to be forced through the swirl chamber and out the nozzle to form a discharge pattern. An adjustable nozzle cap can be used to vary the pattern of the fluid dispensed.

For the piston spray dispenser, as the trigger is released, the spring acts on the piston to return it to its original position. For the bellows spray dispenser, the bellows acts as the spring to return to its original position. This action causes a vacuum in the chamber. The responding fluid acts to close the outlet valve while opening the inlet valve drawing product up to the chamber from the reservoir.

A more complete disclosure of commercially available dispensing devices appears in U.S. Pat. No. 4,082,223, Nozawa, issued Apr. 4, 1978; U.S. Pat. No. 4,161,288, McKinney, issued Jul. 17, 1985; U.S. Pat. No. 4,434,917, Saito et al., issued Mar. 6, 1984; and U.S. Pat. No. 4,819,835, Tasaki, issued Apr. 11, 1989; U.S. Pat. No. 5,303,867, Peterson, issued Apr. 19, 1994; all of said references are incorporated herein by reference.

A broad array of trigger sprayers or finger pump sprayers are suitable for use with the compositions of this invention. These are readily available from suppliers such as Calmar, Inc., City of Industry, Calif.; CSI (Continental Sprayers, Inc.), St. Peters, Mo.; Berry Plastics Corp., Evansville, Ind.—a distributor of Guala® sprayers; or Seaquest Dispensing, Cary, Ill.

The preferred trigger sprayers are the blue inserted Guala® sprayer, available from Berry Plastics Corp., or the Calmar TS800-1A sprayers, available from Calmar Inc., because of the fine uniform spray characteristics, spray volume, and pattern size. Any suitable bottle or container can be used with the trigger sprayer, the preferred bottle is a 17 fl-oz. bottle (about 500 ml) of good ergonomics similar in shape to the Cinch® bottle. It can be made of any materials such as high density polyethylene, polypropylene, polyvinyl chloride, polystyrene, polyethylene terephthalate, glass, or any other material that forms bottles. Preferably, it is made of high density polyethylene or clear polyethylene terephthalate.

For smaller four fl-oz. size (about 118 ml), a finger pump can be used with canister or cylindrical bottle. The preferred pump for this application is the cylindrical Euromist II® from Seaquest Dispensing.

III. METHOD OF USE

The composition herein can be used by distributing, e.g., by placing the aqueous solution into a dispensing means, preferably a spray dispenser and spraying an effective amount onto the desired surface or article. An effective amount as defined herein means an amount sufficient to reduce malodor impression to the point that it is not discernible by the human sense of smell yet not so much as to saturate or create a pool of liquid on said article or surface and so that when dry there is no visual deposit readily discernible. Distribution can be achieved by using a spray device, a roller, a pad, etc.

Preferably, the present invention does not encompass distributing the composition on to shiny surfaces including, e.g., chrome, glass, smooth vinyl, leather, shiny plastic, shiny wood, etc. It is preferable not to distribute the composition onto shiny surfaces because spotting and filming can more readily occur on the surfaces. Furthermore, the composition is for use on inanimate surfaces, i.e., not for use on human skin, because it can cause skin irritation.

The present invention encompasses the method of spraying an effective amount of the composition of the present invention onto household surfaces. Preferably said household surfaces are selected from the group consisting of countertops, cabinets, walls, floors, bathroom surfaces and kitchen surfaces.

The present invention encompasses the method of spraying a mist of an effective amount of the composition of the present invention onto fabric and/or fabric articles. Preferably, said fabric and/or fabric articles include, but are not limited to, clothes, curtains, drapes, upholstered furniture, carpeting, bed linens, bath linens, tablecloths, sleeping bags, tents, car interior, etc.

The present invention encompasses the method of spraying a mist of an effective amount of the composition of the present invention onto and into shoes wherein said shoes are not sprayed to saturation.

The present invention encompasses the method of spraying a mist of an effective amount of the composition of the present invention onto shower curtains.

The present invention relates to the method of spraying a mist of an effective amount of the composition of the present invention onto and/or into garbage cans and/or recycling bins.

The present invention relates to the method of spraying a mist of an effective amount of the composition of the present invention into the air to absorb malodor.

The present invention relates to the method of spraying a mist of an effective amount of the composition of the present invention into and/or onto major household appliances including but not limited to: refrigerators, freezers, washing machines, automatic dryers, ovens, microwave ovens, dishwashers etc., to absorb malodor.

The present invention relates to the method of spraying a mist of an effective amount of the composition of the present invention onto cat litter, pet bedding and pet houses to absorb malodor.

The present invention relates to the method of spraying a mist of an effective amount of the composition of the present invention onto household pets to absorb malodor.

All percentages, ratios, and parts herein, in the Specification, Examples, and Claims are by weight and are approximations unless otherwise stated.

The following are non-limiting examples of the instant composition. Perfume compositions that are used herein are as follows:

| Perfume Ingredients | A Wt. % | B Wt. % | C Wt. % |
| --- | --- | --- | --- |
| 3,7-Dimethyl-6-octenol | 10 | — | 5 |
| Benzyl salicylate | 5 | 20 | 5 |
| Benzyl acetate | 10 | 15 | 5 |
| Benzophenone | 3 | 5 | — |
| Octahydro-3,6,8,8-tetramethyl-1H-3A,7-methanoazulen-6-ol | 2 | — | — |
| 3-Methylene-7-methyl octan-7-ol | 10 | — | 5 |
| Dihydro-nor-cyclopentadienyl acetate | 5 | — | 5 |
| 1,3,4,6,7,8-Hexahydro-4,6,6,7,8,8-hexamethyl-cyclopenta-gamma-2-benzopyrane | 10 | — | — |
| Phenyl ethyl alcohol | 15 | 10 | 20 |
| 3-Hydroxy-3,7-dimethyl-1,6-octadiene acetate | 4 | — | 5 |
| 3-Hydroxy-3,7-dimethyl-1,6-octadiene | 6 | 15 | 5 |
| Methyl dihydro jasmonate | 3 | 10 | 5 |
| 2-Methyl-3(para tert butylphenyl) propionaldehdye | 10 | 15 | 20 |
| Phenyl ethyl acetate | 2 | 5 | 1 |
| 4-Hydroxy-3-methoxybenzaldehyde | — | — | 1 |
| para-Menth-1-en-8-ol, para-menth-len-1-ol | 5 | — | 8 |
| Anisic aldehyde | — | — | 2 |
| Coumarin | — | — | 5 |
| 2-Methyl-3-(para iso propylphenyl)propionaldehyde | — | — | 3 |
| Total | 100 | 100 | 100 |

| Perfume Material | D Wt. % | E Wt. % |
| --- | --- | --- |
| Amyl salicylate | 8 | — |
| Benzyl acetate | 8 | 8 |
| Benzyl Salicylate | — | 2 |
| Citronellol | 7 | 27 |
| Dihydromyrcenol | 2 | — |
| Eugenol | 4 | — |
| Flor acetate | 8 | — |
| Galaxolide | 1 | — |
| Geraniol | 5 | — |
| Hexyl cinnamic aldehyde | 2 | — |
| Hydroxycitronellal | 3 | — |
| Lilial | 2 | — |
| Linalool | 12 | 13 |
| Linalyl acetate | 5 | — |
| Lyral | 3 | — |
| Methyl dihydrojasmonate | 3 | — |
| Nerol | 2 | — |
| Phenoxy ethyl propionate | — | 3 |
| Phenylethyl acetate | 5 | 17 |
| Phenylethyl alcohol | 8 | 17 |
| alpha-Terpineol | 5 | 13 |
| alpha-Terpinene | 5 | — |
| Tetrahydromyrcenol | 2 | — |
| Total | 100 | 100 |

Perfume E is composed of about 70%, by weight, of ingredients having a ClogP of about 3 or smaller.

The following are non-limiting examples of the instant composition.

| Ingredients | Example I Wt. % | Example II Wt. % |
| --- | --- | --- |
| Methylated beta-cyclodextrin | 0.2 | — |
| Hydroxypropyl beta-cyclodextrin | — | 0.2 |
| NaHCO$_3$ | 1.0 | 1.0 |
| Perfume A | 0.02 | — |
| Perfume B | — | 0.02 |
| Distilled water | Balance | Balance |

EXAMPLES I AND II

The ingredients of Examples I and II are mixed and dissolved into clear solutions.

| Ingredients | Example III Wt. % | Example IV Wt. % |
|---|---|---|
| Methylated alpha-cyclodextrin | 0.1 | — |
| Methylated beta-cyclodextrin | 0.1 | — |
| Hydroxypropyl alpha-cyclodextrin | — | 0.11 |
| Hydroxypropyl beta-cyclodextrin | — | 0.29 |
| Propylene glycol | — | 0.025 |
| KHCO$_3$ | 2.0 | 1.0 |
| Perfume C | 0.03 | — |
| Perfume D | — | 0.02 |
| Distilled water | Balance | Balance |

EXAMPLE III

The ingredients of Example III are mixed and dissolved into clear solutions.

EXAMPLE IV

The ingredients of Example IV are mixed and dissolved into clear solutions. Hydroxypropyl alpha-cyclodextrin and hydroxypropyl beta-cyclodextrin are obtained as a mixture with an average degree of substitution of about 4.9, from the hydroxypolylation reaction of a mixture of alpha-cyclodextrin and beta-cyclodextrin. Propylene glycol is a minor by-product (about 6%) of the same reaction.

| Ingredients | Example V Wt. % | Example VI Wt. % |
|---|---|---|
| Methylated beta-cyclodextrin | 0.5 | — |
| Hydroxypropyl beta-cyclodextrin | — | 0.6 |
| Hydroxypropyl gamma-cyclodextrin | — | 0.3 |
| NaHCO$_3$ | 1.0 | 1.5 |
| Perfume E | 0.1 | — |
| Perfume E | — | 0.15 |
| Distilled water | Balance | Balance |

EXAMPLES V AND VI

The ingredients of Examples V and VI are mixed and dissolved into clear solutions. In Example VI, the hydroxypropyl beta-cyclodextrin and hydroxypropyl gamma-cyclodextrin are obtained as a mixture with an average degree of substitution of about 3.8, from the hydroxypolylation reaction of a mixture of beta-cyclodextrin and gamma-cyclodextrin.

| Ingredients | Example VII Wt. % | Example VIII Wt. % |
|---|---|---|
| Methylated beta-cyclodextrin | 0.5 | — |
| Hydroxypropyl-beta-cyclodextrin | — | 0.5 |
| NaHCO$_3$ | 1.0 | 1.0 |
| Perfume E | 0.1 | 0.1 |
| Kathon CG | 0.0008 | 0.0008 |
| Distilled water | Balance | Balance |

EXAMPLES VII AND VIII

The ingredients of Examples VII and VIII are mixed and dissolved into clear solutions.

| Ingredients | Example IX Wt. % | Example X Wt. % |
|---|---|---|
| Methylated beta-cyclodextrin | 0.3 | — |
| Hydroxypropyl-beta-cyclodextrin | — | 0.3 |
| NaHCO$_3$ | 1.0 | 1.0 |
| Perfume D | 0.03 | 0.03 |
| Kathon CG | 0.0008 | 0.0008 |
| Surfynol 465[1] | 0.1 | 0.1 |
| Distilled water | Balance | Balance |

[1]Surfynol 465 ® available from Air Products, has the general structure:

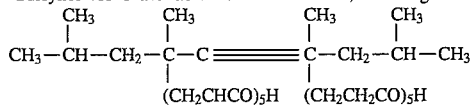

EXAMPLES IX AND X

The ingredients of Examples IX and X are mixed and dissolved into clear solutions.

EXAMPLES XI

The composition of Example IV is sprayed onto clothing using a blue inserted Guala® trigger sprayer, available from Berry Plastics Corp. and allowed to evaporate off of the clothing.

EXAMPLE XII

The composition of Example VII is sprayed onto a kitchen countertop using C Calmar TS 800-1A®, available from Calmar Inc., and wiped off with a paper towel.

EXAMPLE XIII

The composition of Example X is sprayed onto clothes using a cylindrical Euromist II® pump sprayer available from Seaquest Dispensing, and allowed to evaporate off of the clothing.

What is claimed:

1. An aqueous composition for reducing malodor impression, comprising:
   A. from about 0.1% to about 20%, by weight of the composition, of solubilized, water-soluble alkali metal salt selected from the group consisting of carbonate salts, bicarbonate salts, and mixtures thereof,
   B. from about 0.01% to about 1%, by weight of the composition, of perfume;
   C. from about 0.1% to about 5%, by weight of the composition, of solubilized, water-soluble, cyclodextrin;
   D. from about 0.05% to about 3%, by weight of the composition, of solubilizing aid which is a surfactant; and
   E. aqueous carrier; and
   wherein said composition is essentially free of any material that would soil or stain fabric, wherein said composition contains less than 5%, by weight of the composition, of low molecular weight monohydric alcohol, and wherein the pH of said composition is from about 7.5 to about 10.5.

2. The composition of claim 1 wherein said alkali metal salt is present at a level of from about 0.2% to about 10%, by weight of the composition and wherein said perfume is present at a level of from about 0.005% to about 0.2%, by weight of the composition.

3. The composition of claim 2 wherein said alkali metal salt is present at a level of from about 0.3% to about 7%, by weight of the composition and wherein said perfume is present at a level of from about 0.01% to about 0.15%, by weight of the composition.

4. The composition of claim 1 wherein said carbonate salt and said bicarbonate salt are selected from the group consisting of sodium bicarbonate, potassium bicarbonate, potassium carbonate, sodium carbonate, and mixtures thereof.

5. The composition of claim 4 wherein said alkali metal salt is sodium bicarbonate.

6. The composition of claim 1 wherein said solubilizing aid is present at a level of from about 0.05% to about 0.3%, by weight of the composition.

7. The composition of claim 1 wherein said cyclodextrin is present at a level of from about 0.2% to about 4%, by weight of the composition.

8. The composition of claim 7 wherein said cyclodextrin is present at a level of from about 0.3% to about 3%, by weight of the composition.

9. The composition of claim 8 wherein said cyclodextrin solution is present at a level of from about 0.4% to about 2%, by weight of the composition.

10. The composition of claim 1 wherein said water-soluble cyclodextrin is selected from the group consisting of derivatised beta-cyclodextrins, alpha-cyclodextrin and its derivatives, gamma-cyclodextrin and its derivatives, and mixtures thereof.

11. The composition of claim 10 wherein said cyclodextrin derivatives are selected from the group consisting of methyl substituted cyclodextrins, ethyl substituted cyclodextrins, hydroxyl alkyl substituted cyclodextrins, branched cyclodextrins, cationic cyclodextrins, quaternary ammonium cyclodextrins, anionic cyclodextrins, amphoteric cyclodextrins, cyclodextrins wherein at least one glucopyranose unit has a 3-6-anhydro-cyclomalto structure, and mixtures thereof.

12. The composition of claim 10 wherein said cyclodextrin is selected from the group consisting of alpha-cyclodextrin, methylated alpha-cyclodextrin, methylated beta-cyclodextrin, hydroxyethyl alpha-cyclodextrin, hydroxyethyl beta-cyclodextrin, hydroxypropyl alpha-cyclodextrin, hydroxypropyl beta-cyclodextrin, and mixtures thereof.

13. The composition of claim 1 wherein said solubilizing aid is a low-foaming surfactant selected from the group consisting of nonionic surfactants, cationic surfactants, amphoteric surfactants, zwitterionic surfactants, and mixtures thereof.

14. The composition of claim 1 additionally comprising an effective amount of solubilized, water-soluble, antimicrobial preservative having a water-solubility of greater than about 0.3% at room temperature.

15. The composition of claim 1 further comprising water-soluble polymers selected from the group consisting of cationic polymers, anionic polymers, and mixtures thereof.

16. The composition of claim 1 additionally comprising low molecular weight polyol selected from the group consisting of propylene glycol, ethylene glycol, glycerol, and mixtures thereof.

17. An aqueous composition for reducing malodor impression, for use on inanimate surfaces, comprising:
   A. from about 0.3% to about 7%, by weight of the composition, of solubilized, $NaHCO_3$;
   B. from about 0.01% to about 0.5%, by weight of the composition, of perfume;
   C. from about 0.1% to about 5%, by weight of the composition, of solubilized methylated beta-cyclodextrin;
   D. aqueous carrier; and
wherein said composition is essentially free of any material that would soil or stain fabric, wherein said composition contains less than about 3%, by weight of the composition, of low molecular weight monohydric alcohol, and wherein the pH of said composition is from about 7.5 to about 10.5.

18. An aqueous composition for reducing malodor impression, for use on inanimate surfaces, comprising:
   A. from about 0.3% to about 7%, by weight of the composition, of solubilized, $NaHCO_3$;
   B. from about 0.01% to about 0.5%, by weight of the composition, of perfume;
   C. from about 0.1% to about 5%, by weight of the composition, of solubilized hydroxypropyl beta-cyclodextrin;
   D. aqueous carrier; and
wherein said composition is essentially free of any material that would soil or stain fabric, wherein said composition contains less than about 1%, by weight of the composition, of low molecular weight monohydric alcohol, and wherein the pH of said composition is from about 7.5 to about 10.5.

19. An aqueous composition for reducing malodor impression, for use on inanimate surfaces, comprising:
   A. from about 0.3% to about 7%, by weight of the composition, of solubilized, $KHCO_3$;
   B. from about 0.01% to about 0.5%, by weight of the composition, of perfume;
   C. from about 0.1% to about 5%, by weight of the composition, of a mixture of solubilized methylated alpha-cyclodextrin and methylated beta-cyclodextrin;
   D. aqueous carrier; and
wherein said composition is essentially free of any material that would soil or stain fabric, wherein said composition contains less than about 3%, by weight of the composition, of low molecular weight monohydric alcohol, and wherein the pH of said composition is from about 7.5 to about 10.5.

20. An aqueous composition for reducing malodor impression, for use on inanimate surfaces, comprising:
   A. from about 0.3% to about 7%, by weight of the composition, of solubilized, $NaHCO_3$;
   B. from about 0.01% to about 0.5%, by weight of the composition, of perfume;
   C. from about 0.1% to about 5%, by weight of the composition, of solubilized hydroxypropyl beta-cyclodextrin;
   D. from about 0.0001% to about 0.5%, by weight of the composition of solubilized, water-soluble, antimicrobial preservative comprising a mixture of 5-chloro-2-methyl-4-isothiazolin-3-one and 2-methyl-4-isothiazolin-3-one;

E. from about 0.05% to about 0.3%, by weight of the composition, of low-foaming surfactant; and D. aqueous carrier; and wherein said composition is essentially free of any material that would soil or stain fabric, wherein said composition comprises less than about 3%, by weight of the composition, of low molecular weight monohydric alcohol, and wherein the pH of said composition is from about 7.5 to about 10.5.

21. The method of reducing malodor impression on inanimate surfaces, comprising, spraying the composition of claim 1 onto fabric with a trigger-spray device wherein the bottle comprises clear polyethyleneterephthalate.

* * * * *